United States Patent
Honma et al.

(10) Patent No.: US 12,433,153 B2
(45) Date of Patent: Sep. 30, 2025

(54) ORGANIC TRANSISTOR MATERIAL AND ORGANIC TRANSISTOR

(71) Applicants: ORGANO SCIENCE CO., LTD., Omaezaki (JP); USHIO CHEMIX CORPORATION, Kakegawa (JP)

(72) Inventors: Akira Honma, Omaezaki (JP); Hiroyuki Otsuki, Omaezaki (JP); Masanori Tsutsui, Omaezaki (JP); Kazuo Okamoto, Omaezaki (JP)

(73) Assignees: ORGANO SCIENCE CO., LTD., Omaezaki (JP); USHIO CHEMIX CORPORATION, Kakegawa (JP)

( * ) Notice: Subject to any disclaimer, the term of this patent is extended or adjusted under 35 U.S.C. 154(b) by 863 days.

(21) Appl. No.: 17/612,127

(22) PCT Filed: May 25, 2020

(86) PCT No.: PCT/JP2020/020575
§ 371 (c)(1),
(2) Date: Nov. 17, 2021

(87) PCT Pub. No.: WO2020/241582
PCT Pub. Date: Dec. 3, 2020

(65) Prior Publication Data
US 2022/0223792 A1 Jul. 14, 2022

(30) Foreign Application Priority Data
May 27, 2019 (JP) .................................. 2019-098893

(51) Int. Cl.
*H10K 85/60* (2023.01)
*H10K 10/46* (2023.01)

(52) U.S. Cl.
CPC ......... *H10K 85/622* (2023.02); *H10K 10/462* (2023.02); *H10K 85/615* (2023.02); *H10K 85/623* (2023.02); *H10K 85/624* (2023.02); *H10K 85/6574* (2023.02); *H10K 85/6576* (2023.02)

(58) Field of Classification Search
CPC .................................................. H10K 85/622
See application file for complete search history.

(56) References Cited

U.S. PATENT DOCUMENTS

| | | | |
|---|---|---|---|
| 2010/0006830 A1 | 1/2010 | Hong et al. | |
| 2011/0180784 A1 | 7/2011 | Shukla et al. | |
| 2011/0220884 A1 | 9/2011 | Saito et al. | |
| 2014/0081028 A1 | 3/2014 | Hanna et al. | |
| 2015/0166561 A1 | 6/2015 | Kitamura et al. | |
| 2018/0351106 A1 | 12/2018 | Hanna et al. | |

FOREIGN PATENT DOCUMENTS

| | | | | |
|---|---|---|---|---|
| CN | 106565428 A | | 4/2017 | |
| CN | 110903296 A | * | 3/2020 | ........... C07D 493/06 |
| JP | 5314814 B2 | | 10/2013 | |
| JP | 2014-63969 A | | 4/2014 | |
| JP | 5460599 B2 | | 4/2014 | |
| JP | 2018-182056 A | | 11/2018 | |
| TW | 201630916 A | | 9/2016 | |
| WO | WO 2012/121393 A1 | | 9/2012 | |

OTHER PUBLICATIONS

STN-Chemical database registry # 497226-58-1 for 4-(4-pentylcyclohexyl)-4'-(4-propylcyclohexyl)- 1, 1'-Biphenyl, Entered STN: Mar. 10, 2003.*
Online: "http://web.archive.orglweb/20121122033249/http://www.inter chi m .eu/pp.php?ref=7", accessed Oct. 10, 2015.*
International Search Report for PCT/JP2020/020575 mailed on Aug. 11, 2020.
Locklin et al., "Organic Thin Film Transistors Based on Cyclohexyl-Substituted Organic Semiconductors", Chemistry of Materials, 2005, vol. 17, No. 13, pp. 3366-3374.
Written Opinion of the International Searching Authority for PCT/JP2020/020575 (PCT/ISA/237) mailed on Aug. 11, 2020.

* cited by examiner

*Primary Examiner* — David K O'Dell
(74) *Attorney, Agent, or Firm* — Birch, Stewart, Kolasch & Birch, LLP

(57) ABSTRACT

Provided is an organic transistor material characterized by having a trans-1,4-disubstituted cyclohexane structure derived from a compound represented by Formula (1). In Formula (1), X represents a skeleton in which plural phenylene groups or naphthylene groups are linked directly or via a vinyl group, a condensed polycyclic hydrocarbon skeleton, or a heterocyclic compound skeleton; m, n, p, and q each independently represent 0 or 1; and R1 and R2 each independently represent an alkyl group or haloalkyl group having 1 to 15 carbon atoms. This organic transistor material has high carrier mobility and excellent thermal stability.

(1)

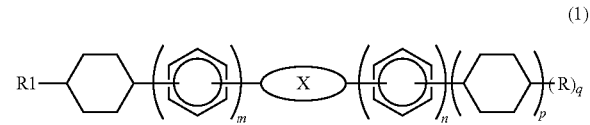

4 Claims, 1 Drawing Sheet

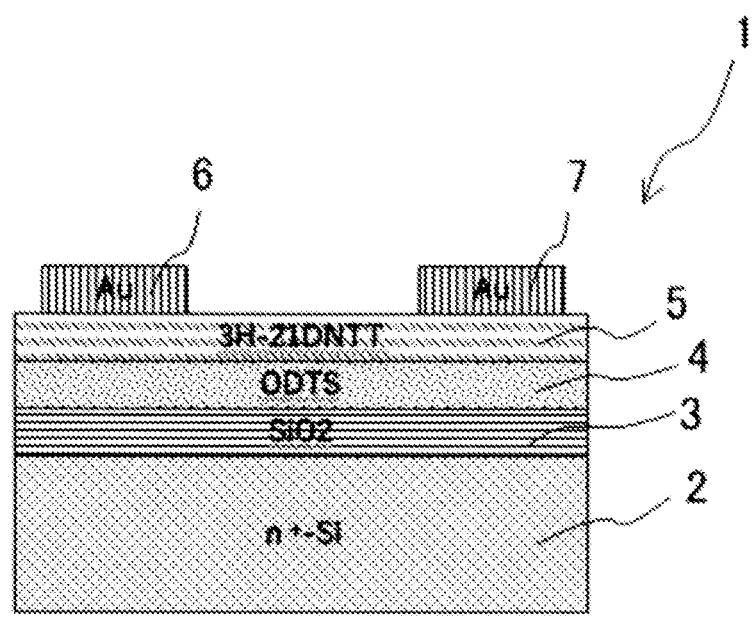

ORGANIC TRANSISTOR MATERIAL AND ORGANIC TRANSISTOR

TECHNICAL FIELD

The present invention relates to: an organic transistor material having high carrier mobility and high thermal stability; and an organic transistor including the same.

BACKGROUND ART

In organic transistors using an organic transistor material as an active layer, not only a dry process such as vapor phase epitaxy but also a wet process such as a printing method can be employed; therefore, such organic transistors can be produced at a lower cost than inorganic transistors such as silicon. Further, by preparing an organic transistor on a plastic substrate, a flexible product can be obtained, which is considered difficult with an inorganic transistor. Accordingly, organic transistors are expected to be applied to, for example, display devices utilizing liquid crystals and display devices utilizing organic EL elements.

Organic transistor materials have been studied and developed for the purpose of improving the carrier mobility, the high-temperature stability and the like, and examples of such organic transistor materials include those having a polyacene skeleton such as pentacene, those having a dibenzanthracene skeleton or a chrysene skeleton (Patent Document 1), those having a thienothiophene skeleton (Patent Document 2), and those having a cyclohexyl group as a substituent (Non-patent Document 1).

RELATED ART DOCUMENTS

Patent Documents

[Patent Document 1] JP5460599B2
[Patent Document 2] JJP5314814B2

Non-Patent Document

[Non-patent Document 1] "Organic Thin Film Transistor Based on Cyclohexyl-Substituted Organic Semiconductors", Chemistry of Materials, 2005, 17, p. 3366-3374

SUMMARY OF THE INVENTION

Problems to be Solved by the Invention

As compared to silicon, organic transistor materials still have room for improvement in terms of carrier mobility and high-temperature stability.

Therefore, an object of the present invention is to provide a novel organic transistor material having high carrier mobility and excellent thermal stability, and an organic transistor.

Means for Solving the Problems

The present inventors intensively studied organic transistor materials to solve the above-described problems, and consequently discovered that a derivative in which a skeleton used in an organic transistor has a cyclohexyl group with an alkyl group side chain as a substituent exhibits high carrier mobility and excellent thermal stability, thereby arriving at the present invention.

The organic transistor material of the present invention is an organic transistor material characterized by having a trans-1,4-cyclohexane structure derived from a compound represented by the following Formula (1):

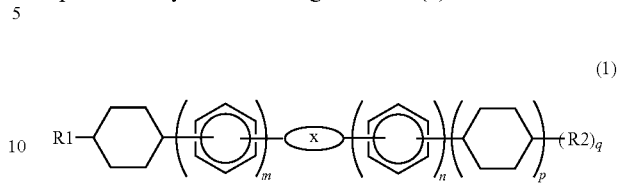

wherein,
X represents a skeleton in which plural phenylene groups or naphthylene groups are linked directly or via a vinyl group, a condensed polycyclic hydrocarbon skeleton, or a heterocyclic compound skeleton;
m, n, p, and q each independently represent 0 or 1; and
R1 and R2 each independently represent an alkyl group or haloalkyl group having 1 to 15 carbon atoms.

In the organic transistor material of the present invention, it is preferred that the X be any one of skeletons represented by the following Formulae (2) to (45):

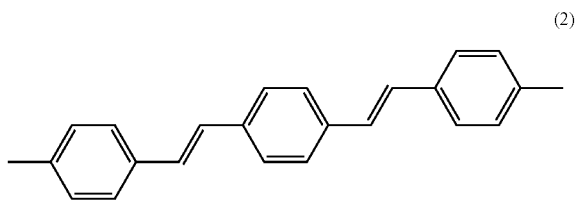

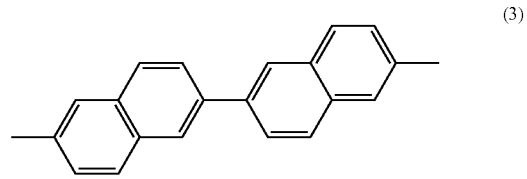

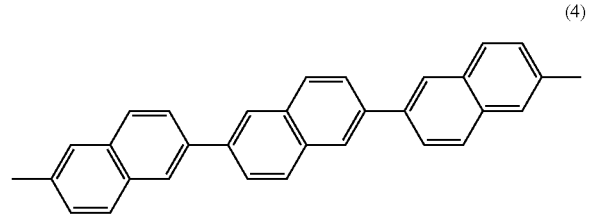

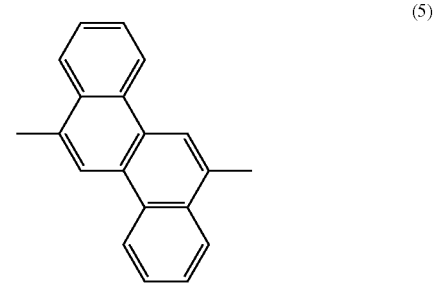

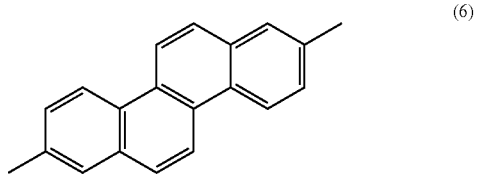

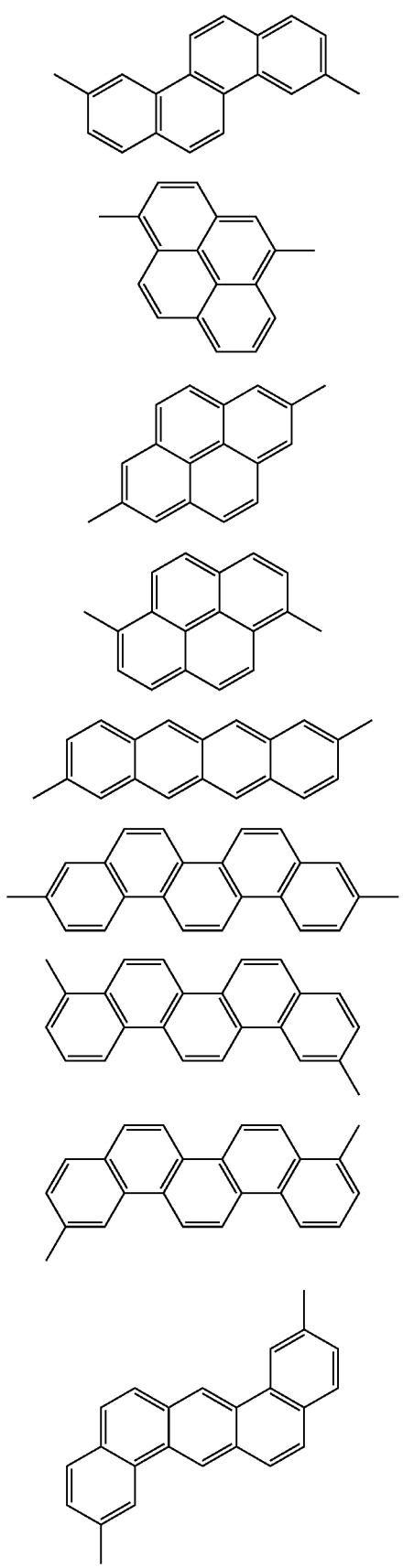
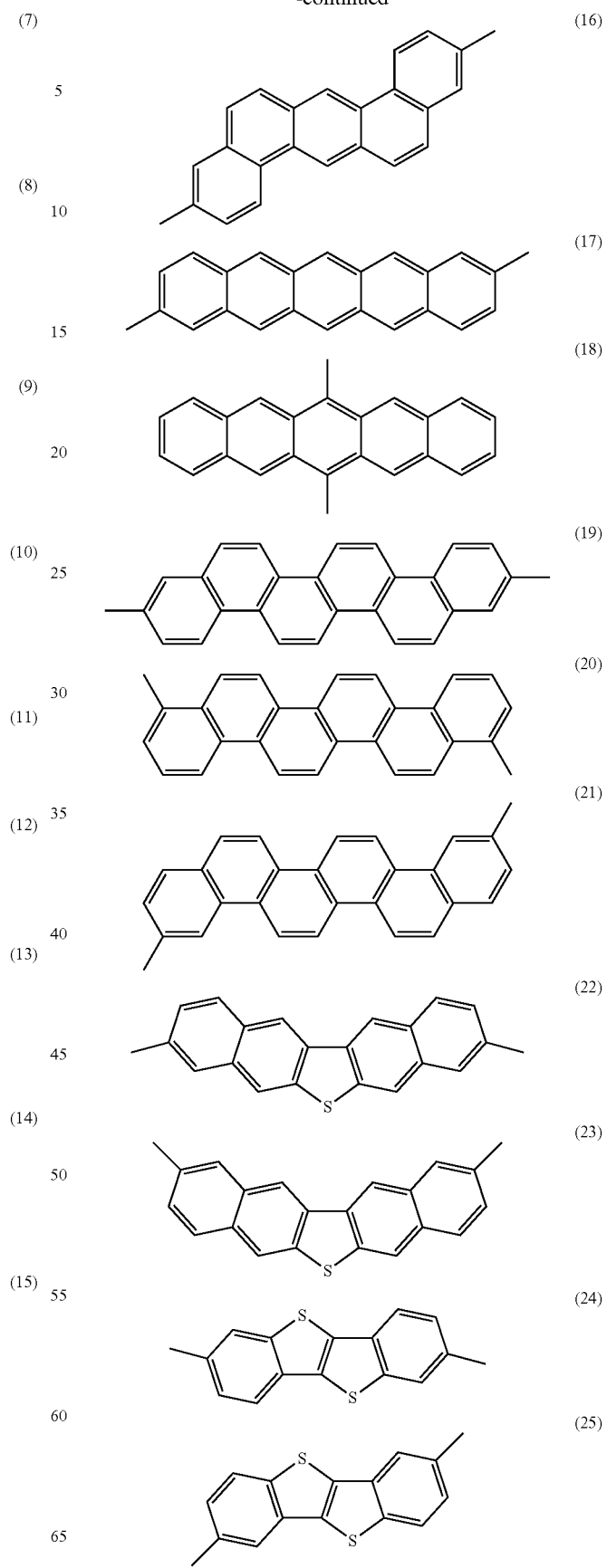

(26)
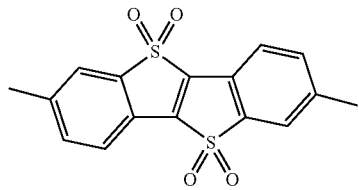
(27)
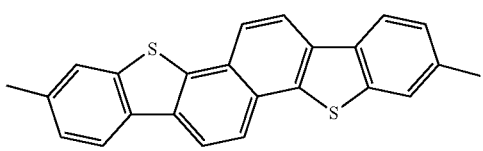
(28)
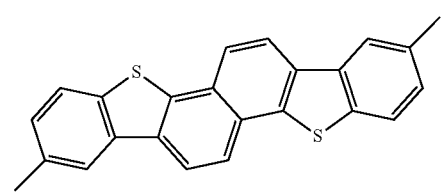
(29)
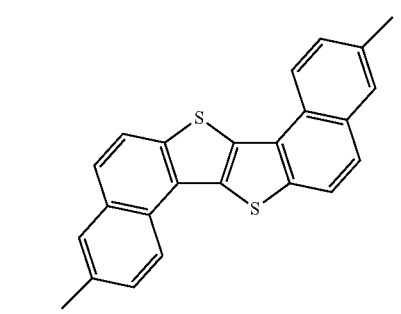
(30)
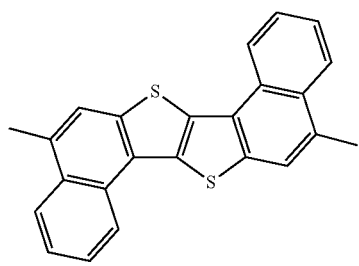
(31)
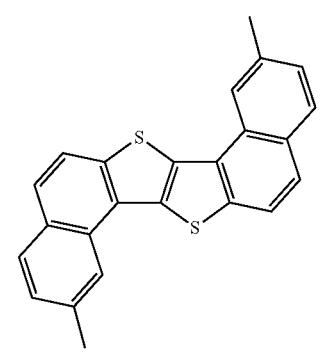
(32)
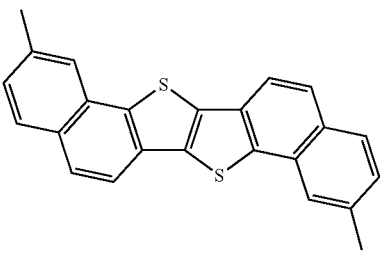
(33)
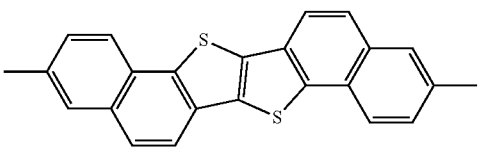
(34)
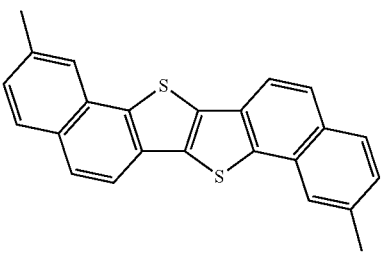
(35)
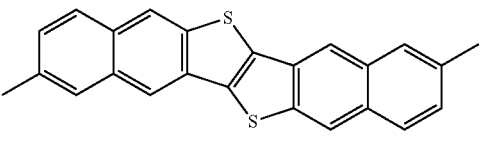
(36)
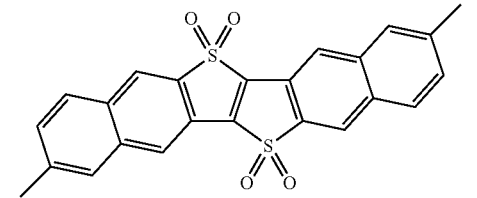
(37)
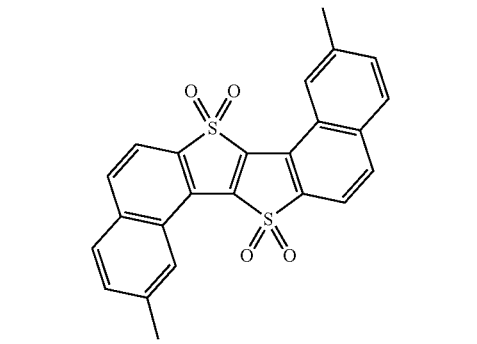
(38)
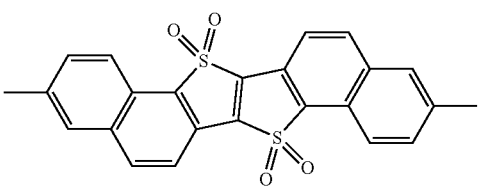

(39)
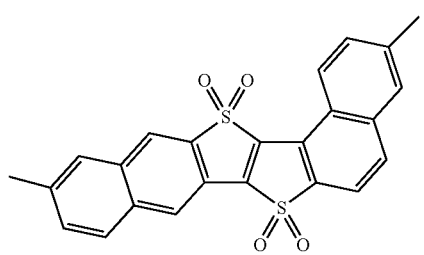

(40)
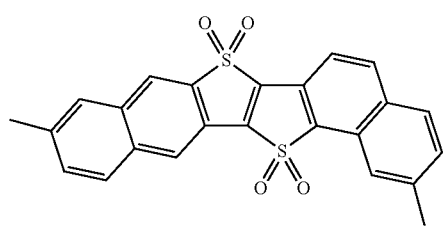

(41)
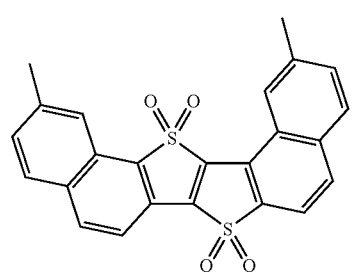

(42)
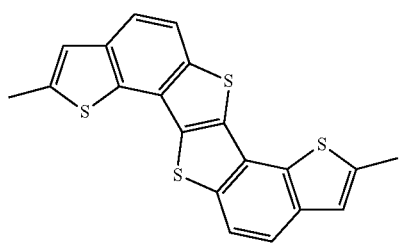

(43)
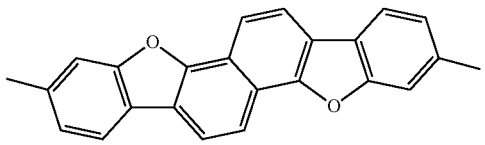

(44)
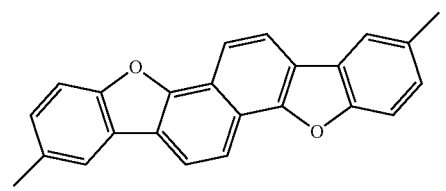

(45)
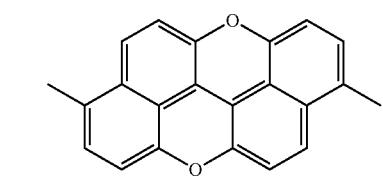

The organic transistor of the present invention contains the above-described organic transistor material.

Effects of the Invention

According to the organic transistor material of the present invention, a novel material having high carrier mobility and excellent stability can be provided.

BRIEF DESCRIPTION OF THE DRAWING

FIG. 1 is a schematic drawing that illustrates an organic transistor produced in Example.

MODE FOR CARRYING OUT THE INVENTION

The organic transistor material of the present invention will now be described more concretely.

The organic transistor material of the present invention is an organic transistor material characterized by having a trans-1,4-disubstituted cyclohexane structure derived from a compound represented by the following Formula (1):

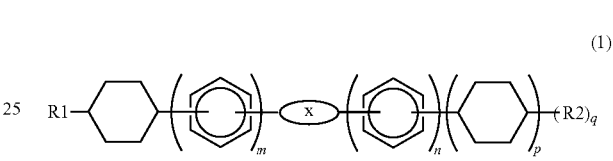

(1)

wherein,
X represents a skeleton in which plural phenylene groups or naphthylene groups are linked directly or via a vinyl group, a condensed polycyclic hydrocarbon skeleton, or a heterocyclic compound skeleton;
m, n, p, and q each independently represent 0 or 1; and
R1 and R2 each independently represent an alkyl group or haloalkyl group having 1 to 15 carbon atoms.

The organic transistor material of the present invention is a derivative in which a skeleton X used as an organic transistor material has a cyclohexyl group, which is a six-membered cycloalkyl group and has an alkyl group or haloalkyl group side chain (such a cyclohexyl group is hereinafter also referred to as "alkylcyclohexyl group"), as a substituent; therefore, the organic transistor material of the present invention exhibits higher carrier mobility and superior thermal stability as compared to conventional organic transistor materials, and has a solubility that allows coating.

The alkyl group constituting a side chain of the alkylcyclohexyl group has 1 to 15, preferably 1 to 10 carbon atoms. The alkyl group may have a straight-chain structure; however, it is optionally branched. Examples of the alkyl group include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, and an n-pentadecyl group. By using an electron-donating alkyl group, not only the solubility in organic solvents can be improved and the molecular arrangement can be controlled but also the wettability to a substrate to be coated can be controlled and the highest occupied molecular orbital (HOMO) level can be increased, allowing the organic transistor material of the present invention to function as a p-type semiconductor.

The side chain may also be a haloalkyl group in which a hydrogen atom of an alkyl group is substituted with a halogen atom. Examples of the halogen atom of the haloalkyl group include a fluorine atom, a chlorine atom, a bromine atom, and an iodine atom. The haloalkyl group may contain one or a plurality of these halogen atoms, and the haloalkyl group preferably contains at least a fluorine atom, more preferably contains only a fluorine atom(s). The halogen atom of the haloalkyl group may substitute some or all of the hydrogen atoms of an alkyl group. Examples of the haloalkyl group include a fluoromethyl group, a 1-fluoromethyl group, a 2-fluoroethyl group, a 2-fluoroisobutyl group, a 1,2-difluoroethyl group, a difluoromethyl group, a trifluoromethyl group, a pentafluoroethyl group, a perfluoroisopropyl group, a perfluorobutyl group, and a perfluorocyclohexyl group. By using an electron-accepting haloalkyl group, the molecular arrangement and the wettability to a substrate to be coated can be controlled and the lowest unoccupied molecular orbital (LUMO) level can be increased, allowing the organic transistor material of the present invention to function as an n-type semiconductor.

The alkylcyclohexyl group and the skeleton X may or may not have a single phenyl group therebetween.

The alkyl group or haloalkyl group of the alkylcyclohexyl group and the skeleton X or the phenyl group are preferably arranged in the 1- and 4-positions of a cyclohexane ring. Further, a trans-form is preferred to a cis-form since it gives superior thermal stability to the organic transistor material.

The skeleton X has at least one alkylcyclohexyl group, and may have two alkylcyclohexyl groups. When there are two alkylcyclohexyl groups, the alkyl group constituting a side chain of a first alkylcyclohexyl group and the alkyl group constituting a side chain of a second alkylcyclohexyl group may have the same number of carbon atoms, or different numbers of carbon atoms. Regardless of whether or not there is a phenyl group between the first alkylcyclohexyl group and the skeleton X, the second alkylcyclohexyl group and the skeleton X may or may not have a single phenyl group therebetween.

The skeleton X is a skeleton used as an organic transistor material, specifically a skeleton in which plural phenylene groups or naphthylene groups are linked directly or via a vinyl group, a condensed polycyclic hydrocarbon skeleton, or a heterocyclic compound skeleton. More specifically, examples of these skeletons include skeletons represented by the below-described Formulae (2) to (45).

[Skeletons in which Plural Phenylene Groups or Naphthylene Groups are Linked Directly or Via Vinyl Group]

(Distyrylbenzene Skeleton)

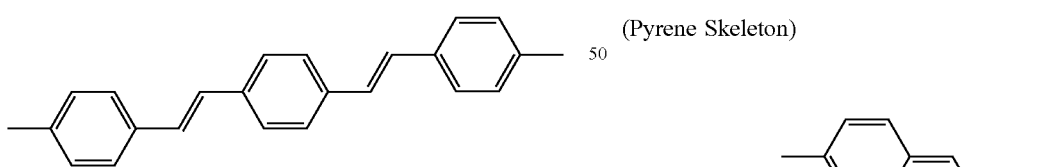

(2)

(Binaphthyl Skeleton)

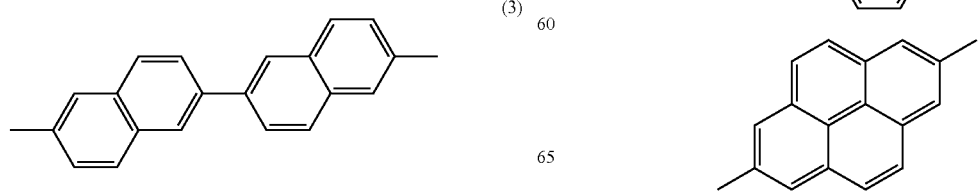

(3)

(Ternaphtyl Skeleton)

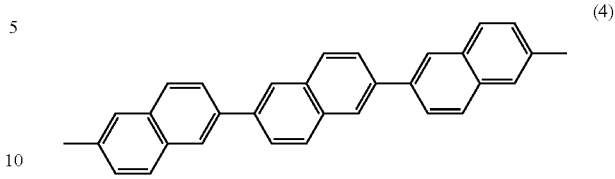

(4)

[Condensed Polycyclic Hydrocarbon Skeletons]

[Condensed Polycyclic Hydrocarbon Skeletons Containing Four Rings]

(Chrysene Skeleton)

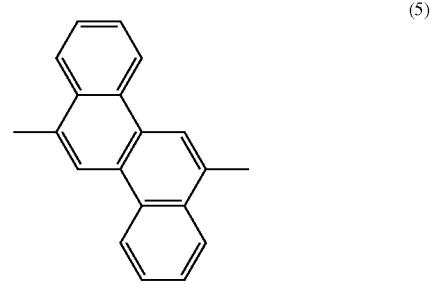

(5)

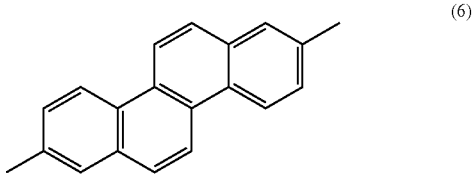

(6)

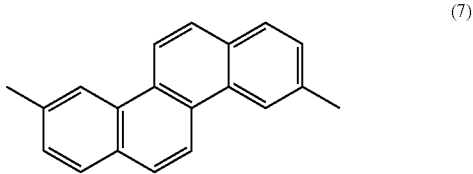

(7)

(Pyrene Skeleton)

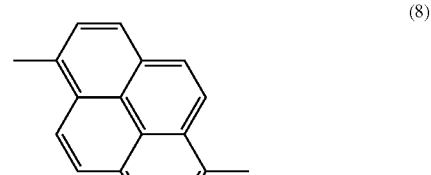

(8)

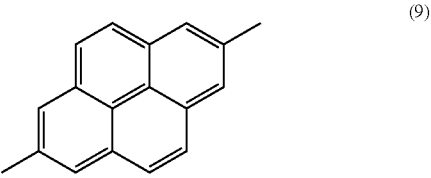

(9)

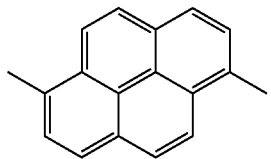
(10)

(Tetracene Skeleton)

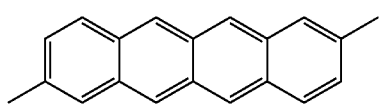
(11)

[Condensed Polycyclic Hydrocarbon Skeletons Containing Five Rings]

(Picene Skeleton)

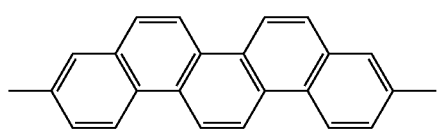
(12)

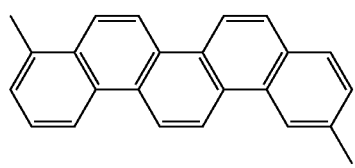
(13)

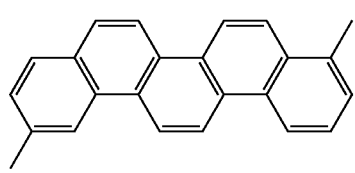
(14)

(Dibenzanthracene Skeleton)

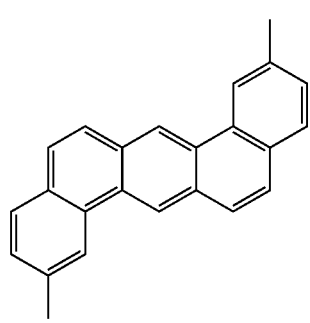
(15)

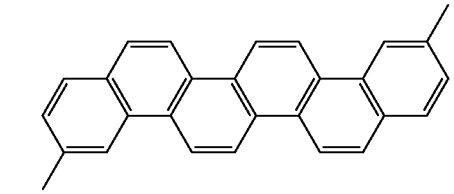
(16)

(Pentacene Skeleton)

(17)

(18)

[Condensed Polycyclic Hydrocarbon Skeletons Containing Six Rings]

(Dibenzochrysene Skeleton)

(19)

(20)

(21)

[Heterocyclic Compound Skeletons]
[Condensed Heterocyclic Compound Skeletons Having One Sulfur Atom-Containing Heterocycle]

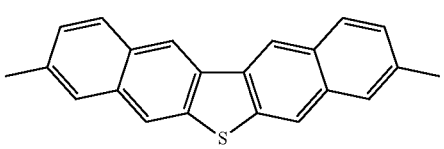
(22)

(23)
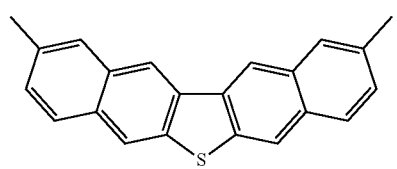
[Condensed Heterocyclic Compound Skeletons Having Two Sulfur Atom-Containing Heterocycles]
(Benzothienobenzothiophene Skeleton; BTBT Skeleton)
(24)
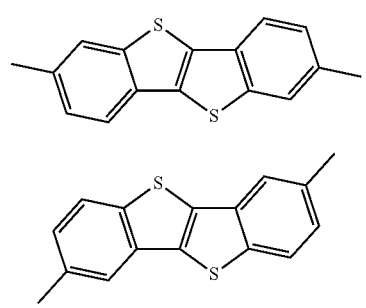
(25)
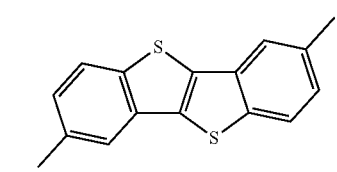
(26)
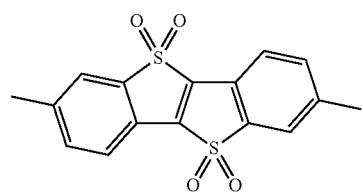
(27)
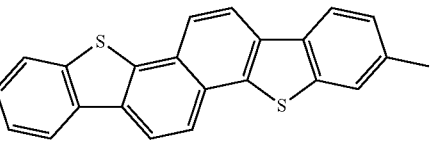
(28)
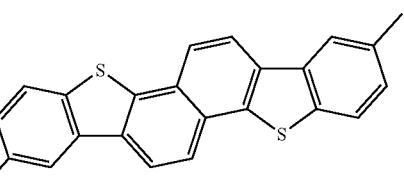
(Dinaphthothienothiophene Skeleton; DNTT skeleton)
(29)
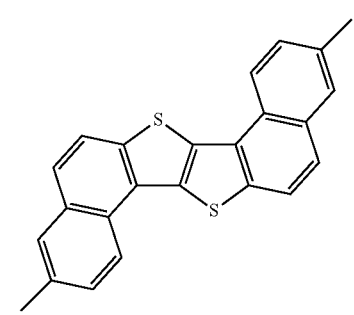
(30)
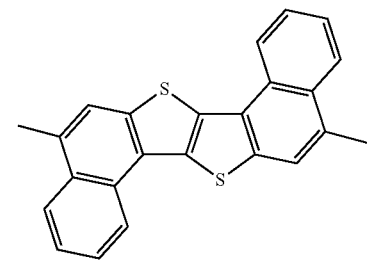
(31)
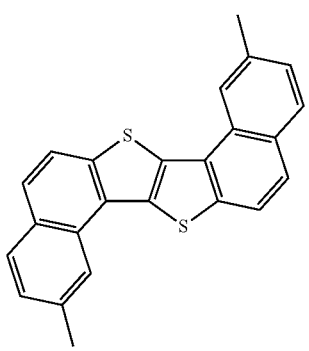
(32)
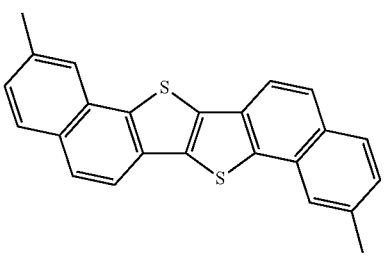
(33)
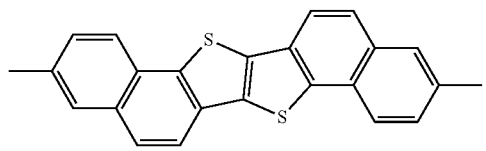
(34)
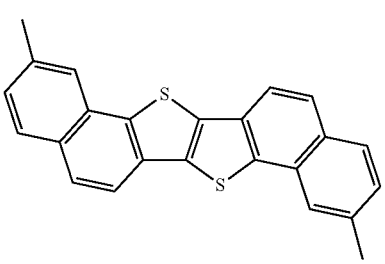
(35)
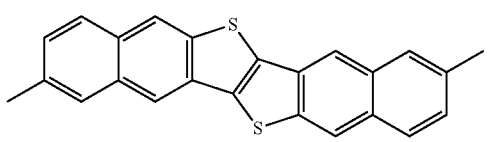
(36)
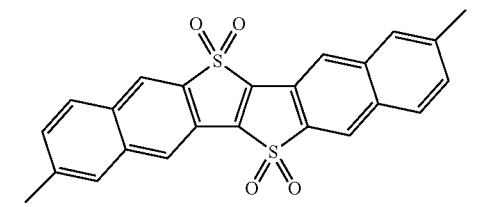

(37)

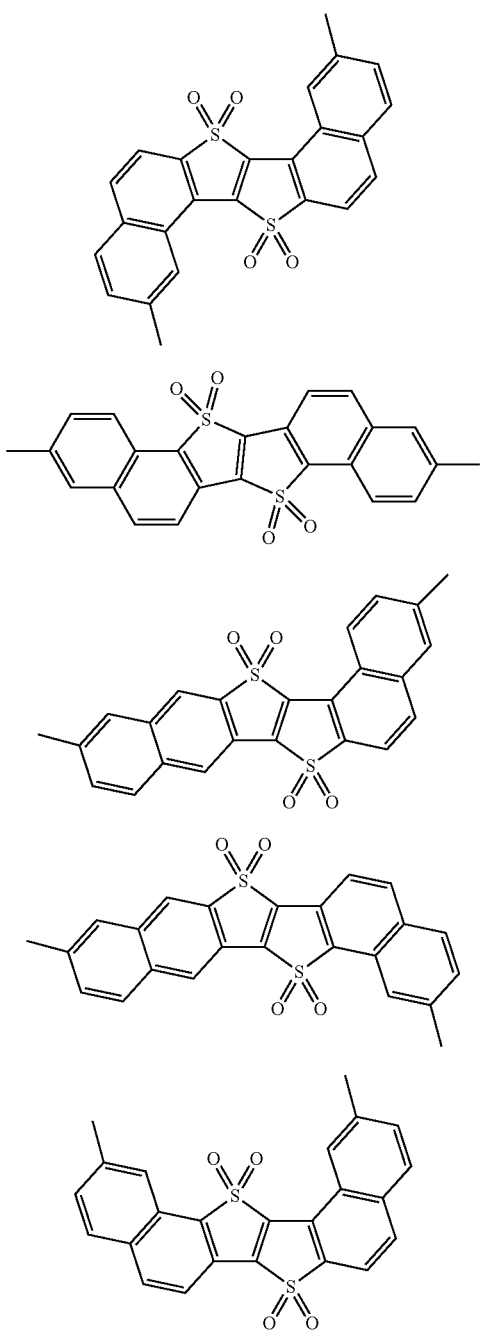

(38)

(39)

(40)

(41)

[Condensed Heterocyclic Compound Skeletons Having Four Sulfur Atom-Containing Heterocycles]
(Di(benzothieno)thienothiophene Skeleton)

(42)

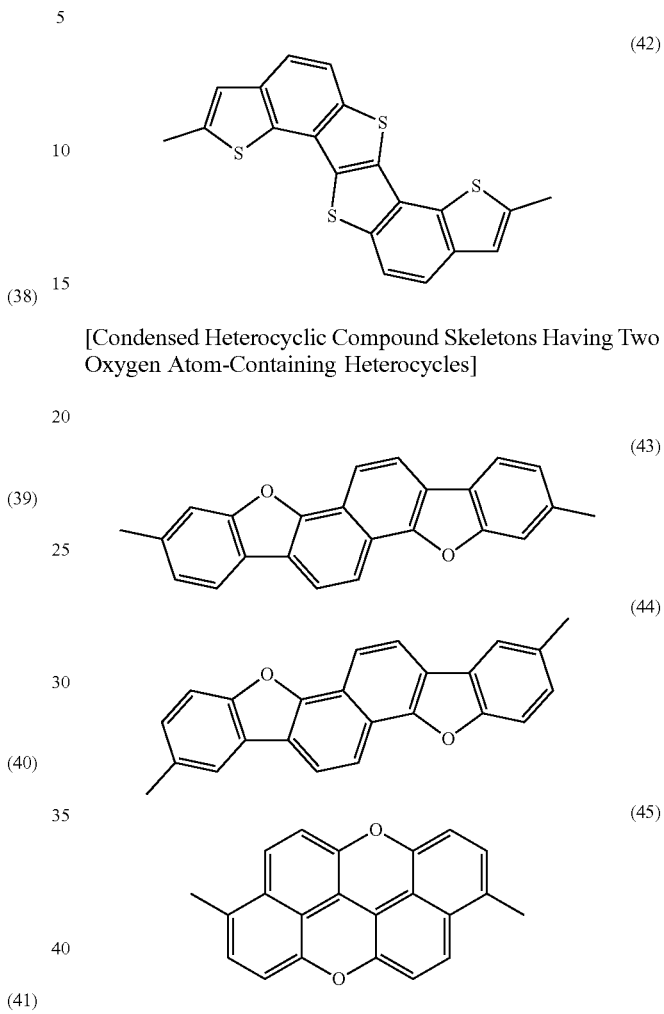

[Condensed Heterocyclic Compound Skeletons Having Two Oxygen Atom-Containing Heterocycles]

(43)

(44)

(45)

Among the above-described skeletons of Formulae (2) to (45), the skeleton X can be, for example, a chrysene skeleton, a benzothienobenzothiophene skeleton, a dibenzanthracene skeleton, or a dinaphthothienothiophene skeleton.

When the skeleton X is the chrysene skeleton of Formula (6), more specific examples of the organic transistor material of the present invention include materials represented by the following Formulae (A-1) to (A-7). In these Formulae, R1 and R2 are each independently an alkyl group or haloalkyl group having 1 to 15 carbon atoms, preferably an alkyl group having 1 to 10 carbon atoms.

(A-1)

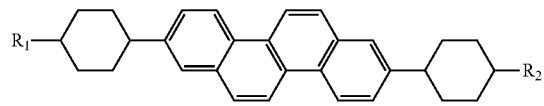

(A-2)

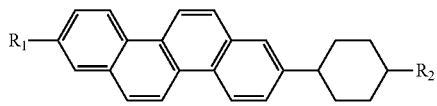

(A-3)

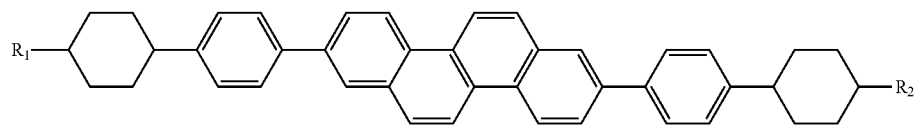

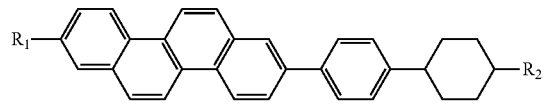
(A-4)

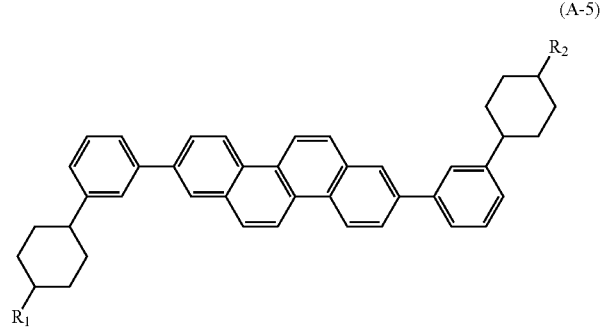
(A-5)

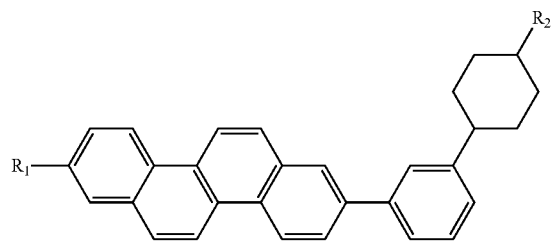
(A-6)

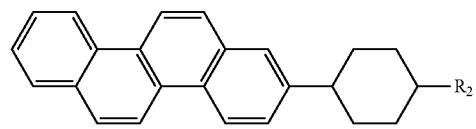
(A-7)

When the skeleton X is the dinaphthothienothiophene skeleton of Formula (29), more specific examples of the organic transistor material of the present invention include materials represented by the following Formulae (B-1) to (B-7). In these Formulae, R1 and R2 are each independently an alkyl group or haloalkyl group having 1 to 15 carbon atoms, preferably an alkyl group having 1 to 10 carbon atoms.

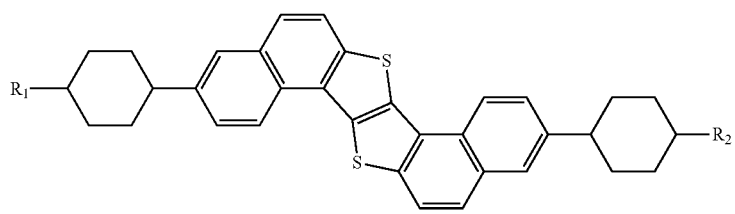
(B-1)

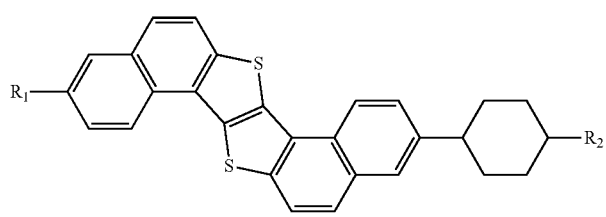
(B-2)

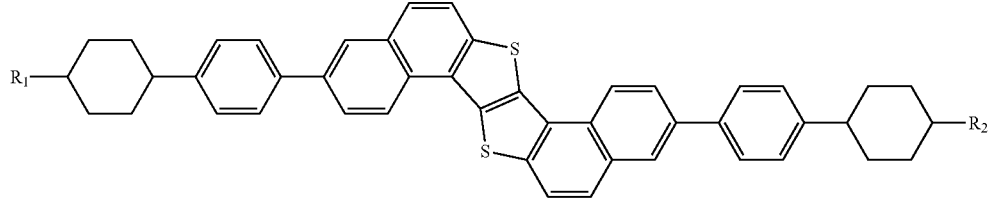
(B-3)

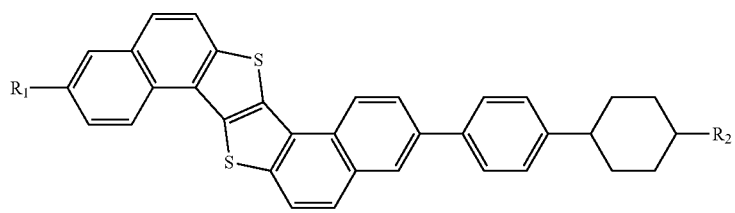
(B-4)

(B-5)

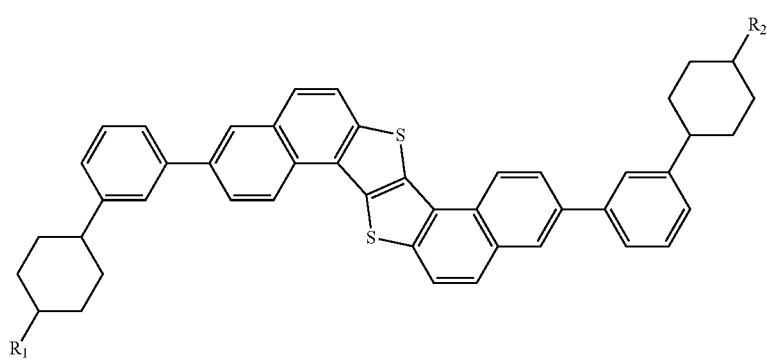

(B-6)

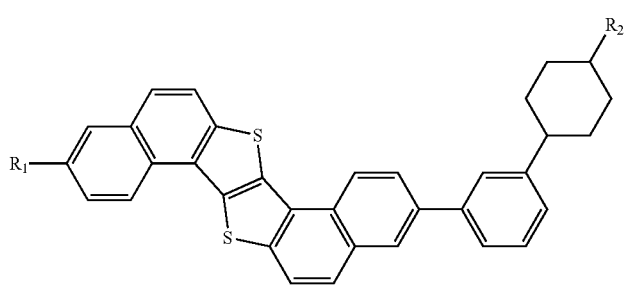

(B-7)

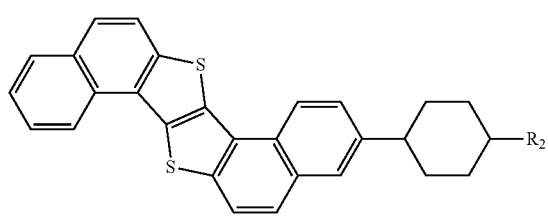

The organic transistor material of the present invention can be synthesized by a known method, examples of which include a Suzuki coupling reaction using a transition metal, a Sonogashira reaction using a copper catalyst, a desilylation reaction, a cyclization reaction using a transition metal, and a Negishi coupling reaction using a transition metal.

The organic transistor of the present invention includes an organic semiconductor layer containing the organic transistor material of the present invention. The organic transistor can have any ordinary structure and is capable of functioning as both a p-type semiconductor and an n-type semiconductor.

For the use in an organic transistor, the organic transistor material of the present invention needs to be purified by removal of impurities and the like so as to improve the purity, and the compound of the present invention can be purified by, for example, a liquid chromatography method, a sublimation method, a zone melting method, a gel permeation chromatography method, or a recrystallization method.

Further, in an organic transistor, the organic transistor material of the present invention is mainly utilized in the form of a thin film, and either a wet process or a dry process may be employed as a method of producing the thin film. The organic transistor material of the present invention can be dissolved in an organic solvent or the like and thereby made suitable for a wet process that has a major industrial advantage.

As the organic solvent, any known organic solvent such as dichloromethane, chloroform, chlorobenzene, dichlorobenzene, cyclohexanol, toluene, xylene, anisole, cyclohexanone, nitrobenzene, methyl ethyl ketone, diglyme, or tetrahydrofuran can be used. When the organic transistor material of the present invention is dissolved in an organic solvent or the like, the temperature and the pressure are not particularly limited; however, the temperature at which the compound of the present invention is dissolved is preferably in a range of 0 to 200° C., more preferably in a range of 10 to 150° C., and the pressure at which the compound of the present invention is dissolved is preferably in a range of 0.1 to 100 MPa, more preferably in a range of 0.1 to 10 MPa. It is also possible to use supercritical carbon dioxide or the like in place of the organic solvent.

The term "wet process" used herein refers to, for example, a spin coating method, a dip coating method, a bar coating method, a spray coating method, an ink-jet coating method, a screen printing method, a planographic printing method, an intaglio printing method, or a relief printing method, and any of these known methods can be employed.

The term "dry process" used herein refers to, for example, a vacuum deposition method, a sputtering method, a CVD method, a laser deposition method, a molecular beam epitaxial growth method, or a vapor-phase transport growth method, and any of these known methods can be employed.

EXAMPLES

The organic transistor material of the present invention will now be described by way of Examples; however, the organic transistor material of the present invention is not limited thereto.

Example 1

A compound 3H-21DNTT shown below was synthesized by the following operations 1 to 4.

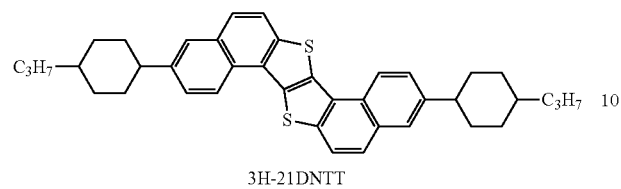

3H-21DNTT

Operation 1

MeO-21DNTT was synthesized according to the following reaction formula:

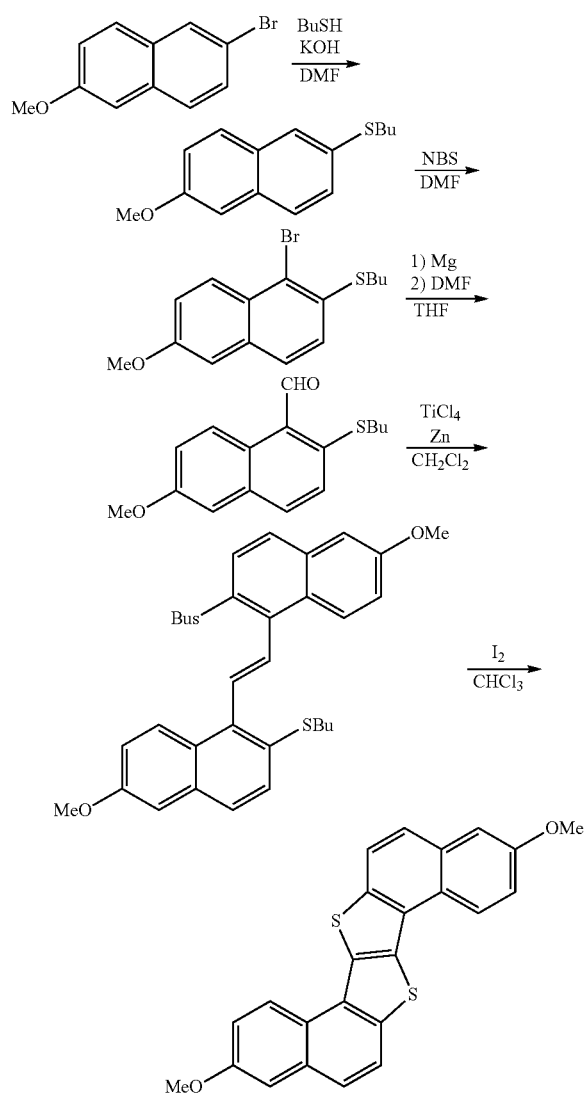

Operation 2

The reaction formula of 21DNTT-OH is shown below.

In a nitrogen atmosphere, 0.10 g (0.25 mmol) of the above-synthesized "MeO-21DNTT" and 20 mL (200 v/w) of anhydrous dichloromethane were added to a 100-mL three-necked flask and cooled to −10° C. Subsequently, 1.5 mL (1.5 mmol, 6 eq) of a 1M BBr$_3$ dichloromethane solution was added dropwise, and the resultant was stirred overnight at 0° C. After the disappearance of the starting materials, 10 mL of water was added dropwise to quench the reaction, and the resulting crystals were filtered, washed with methanol, and then dried under reduced pressure, whereby pale-yellow crystals of "HO-21DNTT" were obtained with a yield of 80%.

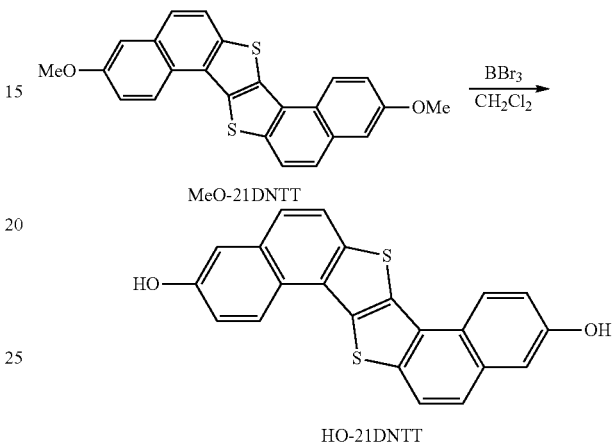

Operation 3

In a nitrogen atmosphere, 75 mg (0.2 mmol) of the thus obtained "HO-21DNTT" and 20 mL (200 v/w) of anhydrous pyridine were added to a 100-mL three-necked flask and cooled to 0° C. Subsequently, 0.34 g (1.2 mmol, 6 eq) of trifluoromethanesulfonic anhydride was added dropwise, and the resultant was stirred overnight at 0° C. After the disappearance of the starting materials was confirmed by HPLC, 10 mL of water was added dropwise to quench the reaction, and the resulting crystals were filtered, washed with methanol, and then dried under reduced pressure, whereby pale-yellow crystals of "TfO-21DNTT" were obtained with a yield of 85%. The reaction formula of this process is shown below:

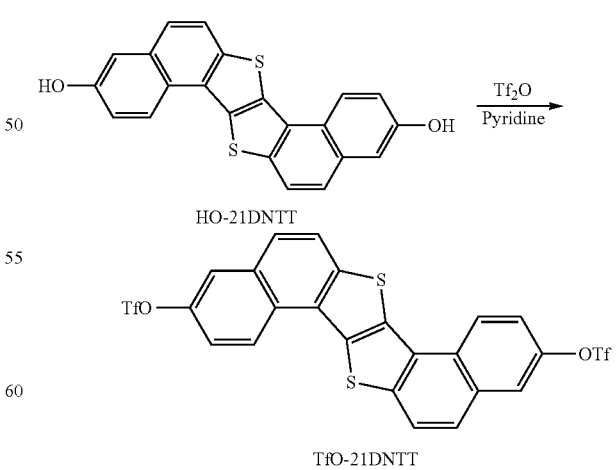

Operation 4

In a nitrogen atmosphere, 0.11 g (0.17 mmol) of the thus obtained "TfO-21DNTT", 6 mg (3 mol %) of Pd(dppf)Cl$_2$, and 10 mL (100 v/w) of toluene were added to a 50-mL three-necked flask, and 5 mL of a THF solution of a Grignard reagent prepared from 0.10 g (0.51 mmol, 3 eq) of 1-bromo-4-propylcyclohexane was further added dropwise at 0° C., followed by overnight stirring at room temperature. After the disappearance of the starting materials was confirmed by HPLC, the resultant was cooled to room temperature, 10 mL of methanol was added thereto dropwise, and the resulting crystals were filtered and washed with acetone. The thus obtained crude product was purified using a silica gel-alumina column containing chlorobenzene as a solvent and subsequently recrystallized with chlorobenzene, and the resulting crystals were dried under reduced pressure, whereby pale-yellow crystals of target compound "3H-21DNTT" were obtained with a yield of 50%.

The physical property data of the thus obtained 3H-21DNTT based on nuclear magnetic resonance ($^1$H NMR) and time-of-flight high-resolution mass spectrometry (TOF HRMS) are shown below.

$^1$H NMR (400 MHz, $C_2D_2Cl_4$, δ ppm): 8.51 (d, 2H), 8.05 (d, 2H), 7.88 (d, 2H), 7.87 (d, 2H), 7.73 (dd, 2H), 2.77 (m, 2H), 1.97-2.12 (m, 8H), 1.67 (m, 4H), 1.43 (m, 6H), 1.31 (m, 4H), 1.20 (m, 4H), 0.98 (t, 6H)

TOF HRMS 589.2965 (calc for $C_{40}H_{44}S_2$ $[M+H]^+$ 589.2954)

Further, the purity determined by high-performance liquid chromatography (HPLC) was 99.973% (@254 nm).

The reaction formula of 3H-21DNTT is shown below:

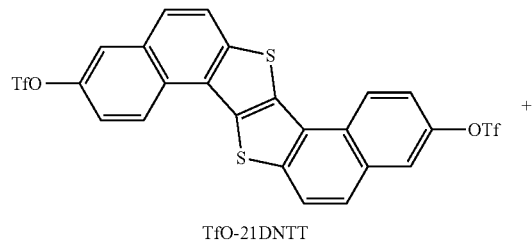

TfO-21DNTT

+

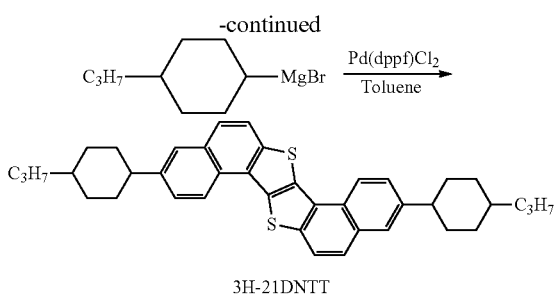

3H-21DNTT

On a silicon wafer on which a 200 nm-thick thermally oxidized film ($SiO_2$) had been formed and which had been treated with ODTS (octadecyltrichlorosilane), 20 nm of 3H-21DNTT was vacuum-deposited at a substrate temperature of 60° C., and 40 nm of gold serving as source and drain electrodes (channel length: 50 channel width: 1.5 mm) was vapor-deposited thereon by an electron beam method, whereby a top contact-type element was produced. This element was heat-treated at 250° C. for 5 minutes and then evaluated.

FIG. 1 is a schematic drawing that illustrates an organic transistor obtained by this vacuum deposition method. An organic transistor 1 illustrated in FIG. 1 has a structure in which an insulating layer 3 made of the thermally oxidized film is formed on a silicon substrate 2 doubling as a gate electrode; a self-assembled monolayer (SAM) 4 made of ODTS is formed on the insulating layer 3; a semiconductor layer 5 made of 3H-21DNTT is formed on the self-assembled monolayer 4; and a source electrode 6 and a drain electrode 7, which are made of gold, are formed with a gap therebetween on the semiconductor layer 5.

According to the results of evaluating the organic transistor, the field-effect mobility measured in vacuum was 2.4 $cm^2V^{-1}s^{-1}$, the on/off current ratio was $10^4$, and the melting point was 310° C.

Example 2

A compound 3HP-28CR shown below was synthesized by the following operations.

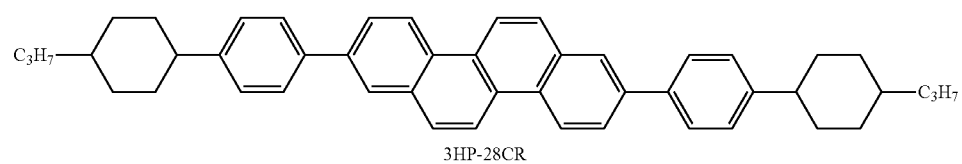

3HP-28CR

In a nitrogen atmosphere, an aqueous potassium carbonate solution and 4-MeTHP were added to "TfO-28CR", 4-(4-propylcyclohexyl)phenylboronic acid and Pd(PPh$_3$)$_4$, and these materials were heated to reflux overnight. After cooling the resultant to room temperature, the resulting crystals were filtered, and the thus obtained crude product was purified by a silica gel-alumina column containing chlorobenzene as a solvent and subsequent heat-washing with toluene, after which the resulting crystals were dried under reduced pressure to obtain a target compound 3HP-28CR. The physical property data of the thus obtained 3HP-28CR based on nuclear magnetic resonance ($^1$H NMR) and time-of-flight high-resolution mass spectrometry (TOF HRMS) are shown below.

$^1$H NMR (400 MHz, C$_2$D$_2$Cl$_4$, δ ppm): 8.85 (dd, 2H), 8.78 (dd, 2H), 8.21 (s, 2H), 8.11 (d, 2H), 8.03 (dd, 2H), 7.77 (d, 4H), 7.41 (d, 4H), 2.62 (m, 2H), 2.06 (m, 4H), 1.97 (m, 4H), 1.40-1.65 (m, 10H), 1.33 (m, 4H), 1.19 (m, 4H), 0.99 (t, 6H)

TOF HRMS (APPI$^+$) 629.4121 (calc for C$_{48}$H$_{52}$ [M+H]$^+$ 629.4142)

The HPLC purity was 100.00% (@254 nm).

The reaction formula of 3HP-28CR is shown below:

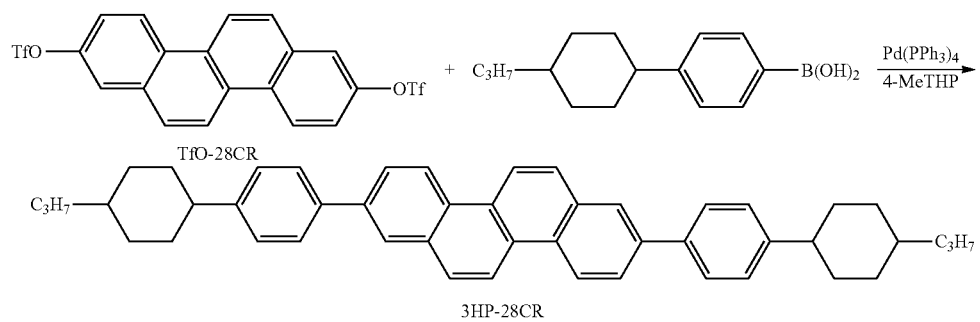

Example 3

A compound 5H-21DNTT shown below was synthesized by the following operations.

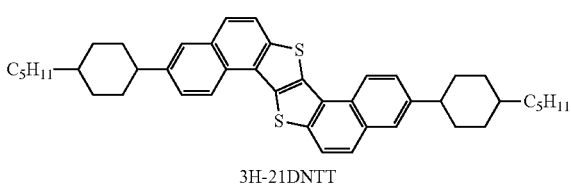

3H-21DNTT

In the operations for synthesizing 5H-21DNTT, a target compound 5H-21DNTT was obtained in the same manner as described above, except that "1-bromo-4-propylcyclohexane" used in the operation 4 was changed to "1-bromo-4-pentylcyclohexane". The physical property data of the thus obtained 5H-21DNTT based on nuclear magnetic resonance ($^1$H NMR) and time-of-flight high-resolution mass spectrometry (TOF HRMS) are shown below.

$^1$H NMR (400 MHz, C$_2$D$_2$Cl$_4$, δ ppm): 8.51 (d, 2H), 8.05 (d, 2H), 7.89 (s, 2H), 7.87 (d, 2H), 7.73 (dd, 2H), 2.77 (m, 2H), 1.98-2.12 (m, 8H), 1.33-1.98 (m, 20H), 1.22 (m, 4H), 0.96 (t, 6H)

TOF HRMS (APPI$^+$) 645.3575 (calc for C$_{44}$H$_{52}$S$_2$ [M+H]$^+$ 645.3580)

The HPLC purity was 99.958% (@254 nm).

An organic transistor was produced by a vapor deposition method using the thus obtained 5H-21DNTT, and the mobility thereof was found to be 3.08 cm$^2$/Vs. Further, the thus-obtained target compound had an intermediate phase (liquid-crystal phase) at 242 to 288° C. during heating.

Example 4

A compound 7H-21DNTT shown below was synthesized by the following operations.

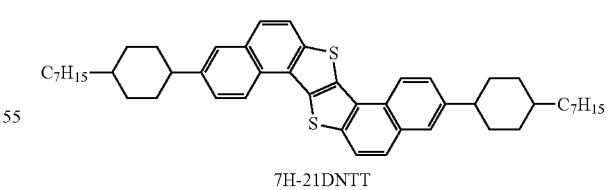

7H-21DNTT

In the operations for synthesizing 7H-21DNTT, a target compound 7H-21DNTT was obtained in the same manner as described above, except that "1-bromo-4-propylcyclohexane" used in the operation 4 was changed to "1-bromo-4-heptylcyclohexane". The physical property data of the thus obtained 7H-21DNTT based on nuclear magnetic resonance ($^1$H NMR) and time-of-flight high-resolution mass spectrometry (TOF HRMS) are shown below.

¹H NMR (400 MHz, CDCl₃, δ ppm): 8.51 (d, 2H), 8.05 (d, 2H), 7.89 (s, 2H), 7.87 (d, 2H), 7.73 (dd, 2H), 2.77 (m, 2H), 1.98-2.12 (m, 8H), 1.68 (m, 4H), 1.30-1.45 (m, 26H), 1.21 (m, 4H), 0.95 (t, 6H)

TOF HRMS(APPI⁺) 701.4096 (calc for $C_{48}H_{60}S_2$ [M+H]⁺ 701.4215)

The HPLC purity was 99.888% (@254 nm).

Using the thus obtained 7H-21DNTT, an organic transistor was produced by a vacuum deposition method under the same conditions as in Example 1, except that the heat treatment of the operation 5 was performed at 160° C. for 5 minutes. The field-effect mobility was 1.27 $cm^2V^{-1}s^{-1}$, and the on/off current ratio was $10^8$. Further, the thus obtained target compound had an intermediate phase (liquid-crystal phase) at 160 to 257° C. during heating.

Example 5

A compound 4H-BTBT shown below was synthesized by the following operations.

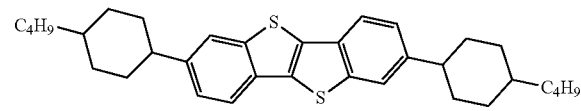

As the operations for synthesizing 4H-BTBT, $PdCl_2$ (dppf) and toluene were added to 2,7-ditriflate-[1]benzothieno[3,2-b][1]benzothiophene in a nitrogen atmosphere, a Grignard reagent prepared from 1-bromo-4-propylcyclohexane was further added dropwise at 0° C., and the resultant was heated to room temperature and stirred overnight. The thus obtained crude product was purified using a silica gel-alumina column containing toluene as a solvent and subsequently recrystallized with toluene, and the resulting crystals were dried under reduced pressure, whereby a target compound 4H-BTBT was obtained. The physical property data of the thus obtained 4H-BTBT based on nuclear magnetic resonance (¹H NMR) and time-of-flight high-resolution mass spectrometry (TOF HRMS) are shown below.

¹H NMR (400 MHz, CDCl₃, δ ppm): 7.76 (d, 2H), 7.73 (s, 2H), 7.30 (dd, 2H), 2.62 (m, 2H), 1.95 (m, 8H), 1.49-1.59 (m, 4H), 1.26-1.33 (m, 14H), 1.10 (m, 4H), 0.92 (t, 6H)

TOF HRMS (APPI⁺) 516.3116 (calc for $C_{34}H_{44}S_2$ [M+H]⁺ 516.2884)

The HPLC purity was 99.983% (@254 nm).

The reaction formula of 4H-BTBT is shown below:

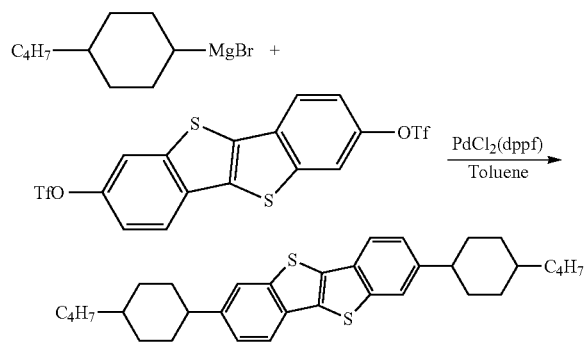

Using the thus obtained 4H-BTBT, a thin film was produced from an anisole solution by an edge casting method at a substrate temperature of 45° C.

<Production of Thin-Film Field-Effect Transistor>

On the thus obtained thin film, 2 nm of 2,3,5,6-tetrafluoro-7,7,8,8-tetracyanoquinodimethane and 30 nm of gold were vapor-deposited as an acceptor and an electrode, respectively, using a mask designed to give a channel length of 100 μm. As an insulating layer, a 200 nm-thick thermally oxidized film ($SiO_2$) was used. The transfer characteristics were measured using a 4200-SCS semiconductor parameter analyzer manufactured by Keithley Instruments, Inc. The mobility was estimated from the thus measured transfer characteristics. The thus estimated field-effect mobility was 4.8 $cm^2$/Vs. Further, the above-obtained target compound had an intermediate phase (liquid-crystal phase) at 77 to 239° C. during heating and at 72 to 225° C. during cooling.

Example 6

Using "3H-21DNTT" synthesized in Example 1, a thin film was produced from a 3-chlorothiophene solution in the same manner as in Example 5 by an edge casting method at a substrate temperature of 40° C. The field-effect mobility was estimated to be 8.8 $cm^2$/Vs.

Example 7

<Production of Thin-Film Field-Effect Transistor>

On a glass substrate, 50 nm of Al was vacuum-deposited to form a gate electrode. On this gate electrode, a 480 nm-thick gate insulating film was formed using parylene C. On the substrate on which 50 nm of Au was vacuum-deposited to form source and drain electrodes, a thin film was produced from an o-dichlorobenzene solution by a drop casting method at a substrate temperature of 65° C., using "5H-21DNTT" synthesized in Example 3. The transfer characteristics were measured using a 4200-SCS semiconductor parameter analyzer manufactured by Keithley Instruments, Inc. The mobility was estimated from the thus measured transfer characteristics.

The thus estimated field-effect mobility was 14.1 $cm^2$/Vs.

Example 8

Using "7H-21DNTT" synthesized in Example 4, a thin film was produced from a 3-chlorothiophene solution in the same manner as in Example 5 by an edge casting method at a substrate temperature of 40° C. The field-effect mobility was estimated to be 4.4 $cm^2$/Vs.

Example 9

A compound 2H-DBA shown below was synthesized by the following operations 1 to 3.

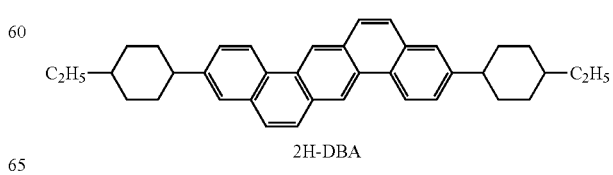

2H-DBA

Operation 1

The reaction formula of a compound (b) is shown below:

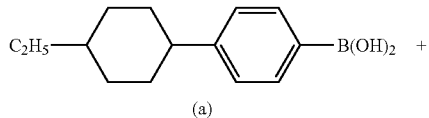

(a)

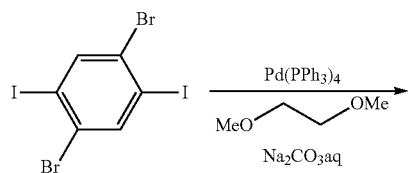

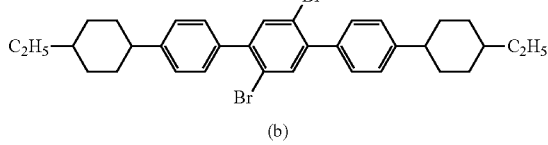

(b)

In a nitrogen atmosphere, 6.8 g (29.5 mmol) of a compound (a) (manufactured by Sigma-Aldrich Co., LLC.), 5.7 g (11.8 mmol) of dibromodiiodobenzene (manufactured by Tokyo Chemical Industry Co., Ltd.), 0.68 g (0.59 mmol) of tetrakis(triphenylphosphine)palladium(0), and 500 ml of dimethoxyethane were placed in a reaction vessel, and 100 ml of an aqueous solution containing 6.2 g (59.8 mmol) of sodium carbonate was added thereto. The resulting reaction mixture was heated to reflux at 70° C. for 12 hours. This reaction mixture was filtered and then washed with water and methanol, whereby 4.3 g of the compound (b) was obtained (yield: 60%).

Operation 2

The reaction formula of a compound (c) is shown below:

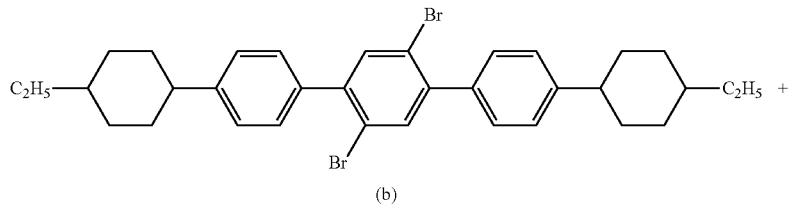

(b)

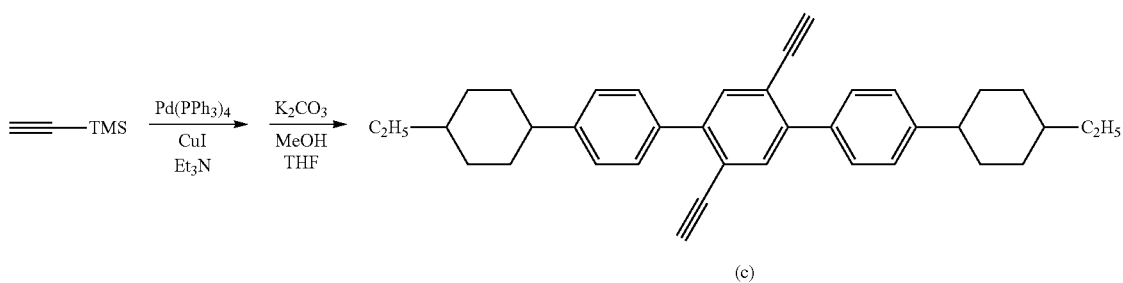

(c)

In a nitrogen atmosphere, 4.3 g (7.1 mmol) of the compound (b), 0.82 g (0.7 mmol) of tetrakis(triphenylphosphine)palladium(0), 0.27 g (1.4 mmol) of copper (I) iodide and 100 ml of triethylamine were placed in a reaction vessel, and 1.5 g (15.5 mmol) of trimethylsilylacetylene was added thereto. The resulting reaction mixture was heated to reflux at 80° C. for 14 hours. This reaction mixture was washed with methanol and heptane. The thus obtained crude product and 2.6 g (19.1 mmol) of potassium carbonate were placed in a reaction vessel, and methanol, THF and water were added thereto. These materials were stirred at room temperature for 8 hours. The resulting reaction mixture was filtered, and the filtrate was washed with saline, followed by solvent removal by vacuum distillation. The thus obtained crude product was purified using a silica gel-alumina column containing heptane and ethyl acetate as solvents, whereby 2.8 g of the compound (c) was obtained (yield: 81%).

Operation 3

The reaction formula of 2H-DBA is shown below:

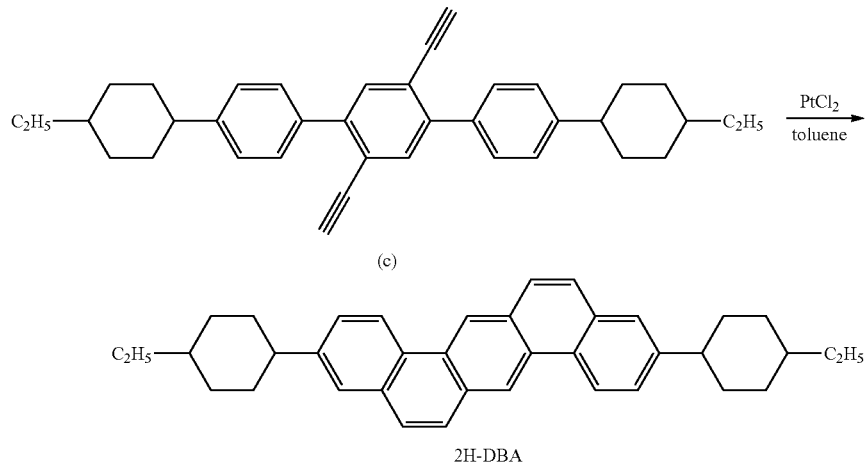

In a nitrogen atmosphere, 2.8 g (5.7 mmol) of the compound (c) and 0.08 g (0.3 mmol) of platinum chloride were placed in a reaction vessel, and 150 ml of toluene was added thereto. The resulting reaction mixture was heated to reflux at 120° C. for 24 hours. This reaction mixture was filtered and then washed with dichloromethane. The thus obtained crude product was purified by sublimation, whereby 1.0 g of 2H-DBA was obtained (yield: 35%).

$^1$H NMR (400 MHz, $C_2D_2Cl_4$, δ ppm): 9.11 (s, 2H), 8.79 (d, 2H), 7.97 (d, 2H), 7.75 (td, 4H), 7.63 (dd, 2H), 2.75 (tt, 2H), 2.10 (d, 4H), 1.99 (d, 4H), 1.66 (m, 4H), 1.35 (m, 6H), 1.18 (m, 4H), 0.99 (t, 6H)

TOF HRMS (APPI+) 499.3370 (calc for $C_{38}H_{42}$ [M+H]+ 499.3359)

Using the thus obtained "2H-DBA", a thin film was produced from a toluene solution in the same manner as in Example 5 by an edge casting method at a substrate temperature of 70° C. The field-effect mobility was estimated to be 8.1 cm$^2$/Vs.

Example 10

A compound 3H-DBA shown below was synthesized by the same operations as in Example 9, except that the compound (a) was changed to a compound (d) (manufactured by Sigma-Aldrich Co., LLC.) shown below.

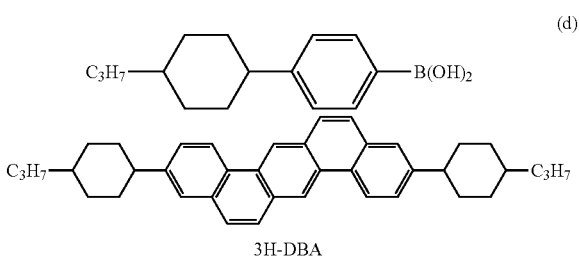

$^1$H NMR (400 MHz, $C_2D_2Cl_4$, δ ppm): 9.11 (s, 2H), 8.79 (d, 2H), 7.96 (d, 2H), 7.75 (td, 4H), 7.63 (dd, 2H), 2.76 (tt, 2H), 2.11 (d, 4H), 1.99 (d, 4H), 1.67 (m, 4H), 1.46 (m, 4H), 1.33 (m, 4H), 1.19 (m, 4H), 0.99 (t, 6H)

Using the thus obtained "3H-DBA", a thin film was produced from a toluene solution in the same manner as in Example 5 by an edge casting method at a substrate temperature of 60° C. The field-effect mobility was estimated to be 8 cm$^2$/Vs.

Example 11

A compound 4H-DBA shown below was synthesized by the same operations as in Example 9, except that the compound (a) was changed to a compound (e) shown below.

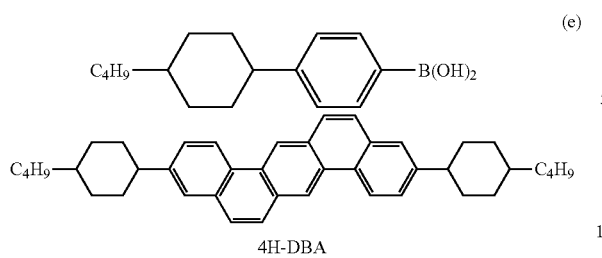

4H-DBA $^1$H NMR (400 MHz, $C_2D_2Cl_4$, δ ppm): 9.10 (s, 2H), 8.79 (d, 2H), 7.96 (d, 2H), 7.75 (td, 4H), 7.63 (dd, 2H), 2.75 (tt, 2H), 2.09 (d, 4H), 1.98 (d, 4H), 1.67 (m, 4H), 1.31-1.39 (m, 12H), 1.19 (m, 4H), 0.97 (t, 6H)

Using the thus obtained "4H-DBA", a thin film was produced from an anisole solution in the same manner as in Example 5 by an edge casting method at a substrate temperature of 90° C. The field-effect mobility was estimated to be 8.5 cm$^2$/Vs. Further, the above-obtained target compound had an intermediate phase (liquid-crystal phase) at 254 to 341° C. during heating and at 246 to 335° C. during cooling.

DESCRIPTION OF SYMBOLS

1: organic transistor
2: silicon substrate
3: insulating layer
4: self-assembled monolayer
5: semiconductor layer
6: source electrode
7: drain electrode

The invention claimed is:

1. An organic transistor material, characterized by having a trans-1,4-disubstituted cyclohexane structure derived from a compound represented by the following Formula (1):

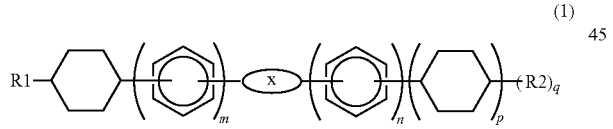

wherein, m, n, p, and q each independently represent 0 or 1;

R1 and R2 each independently represent an alkyl group or haloalkyl group having 1 to 15 carbon atoms; and X is any one of skeletons represented by the following Formulae (2) to (44):

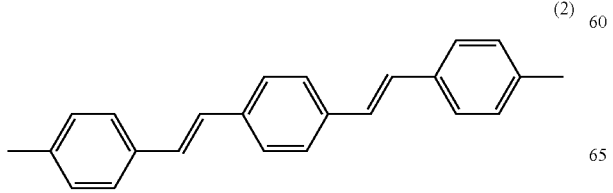

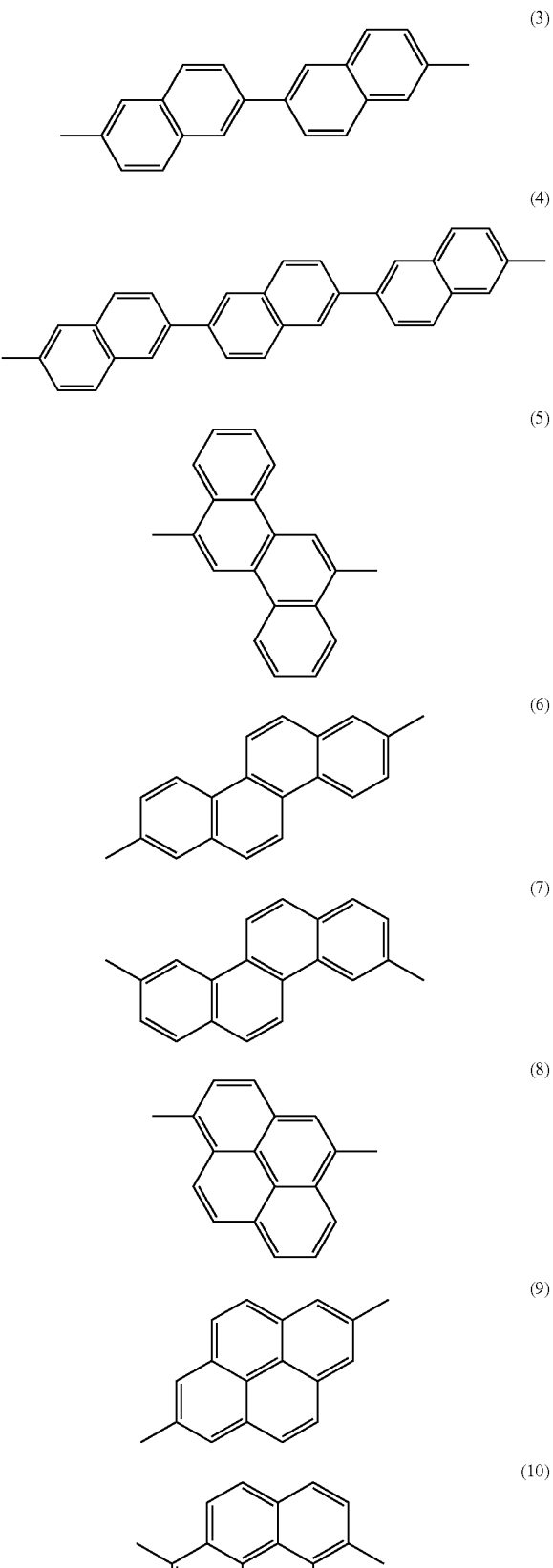

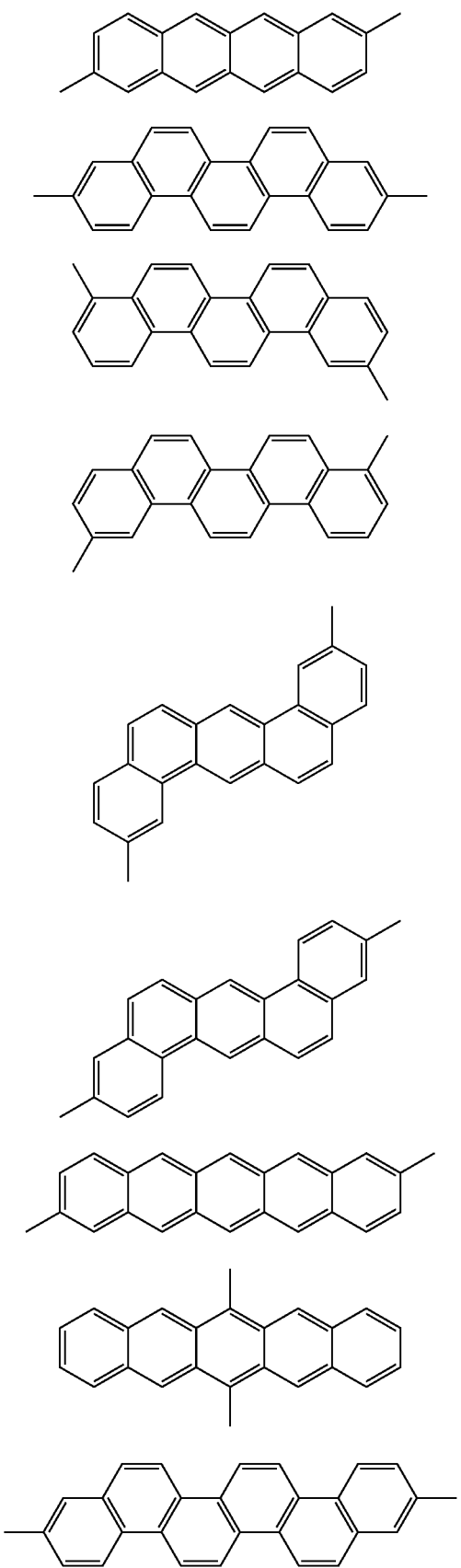
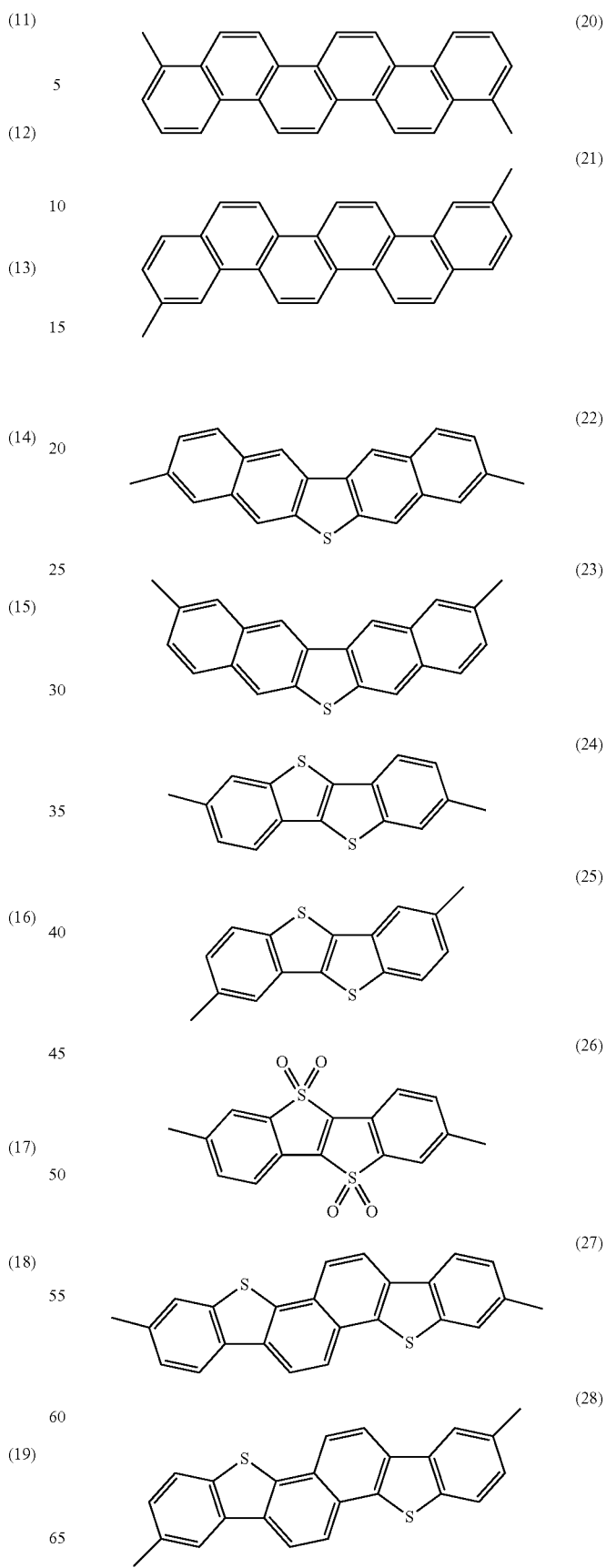

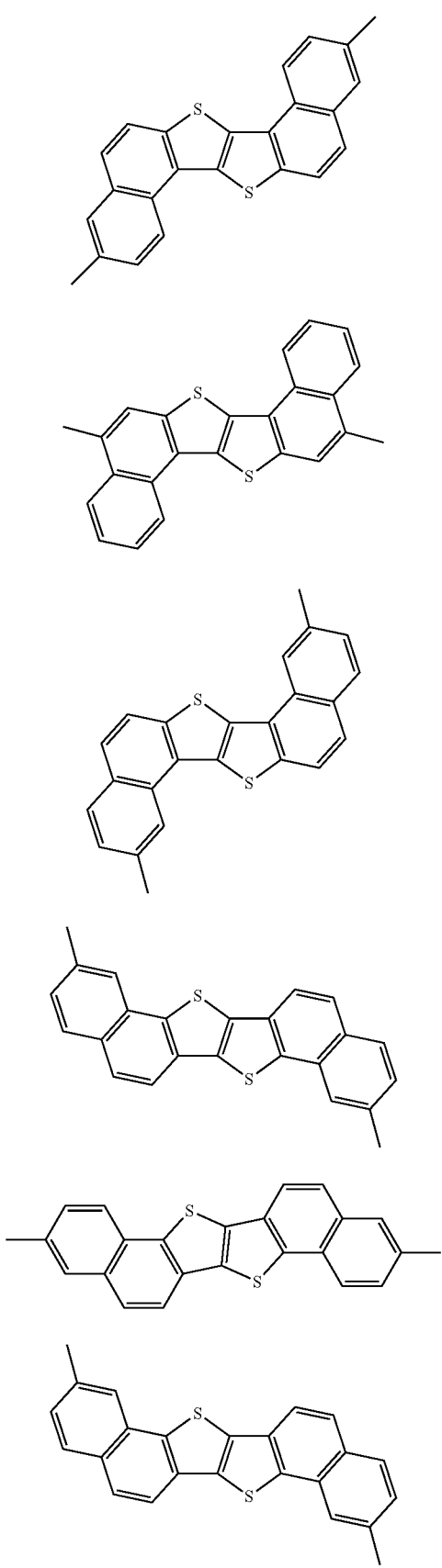
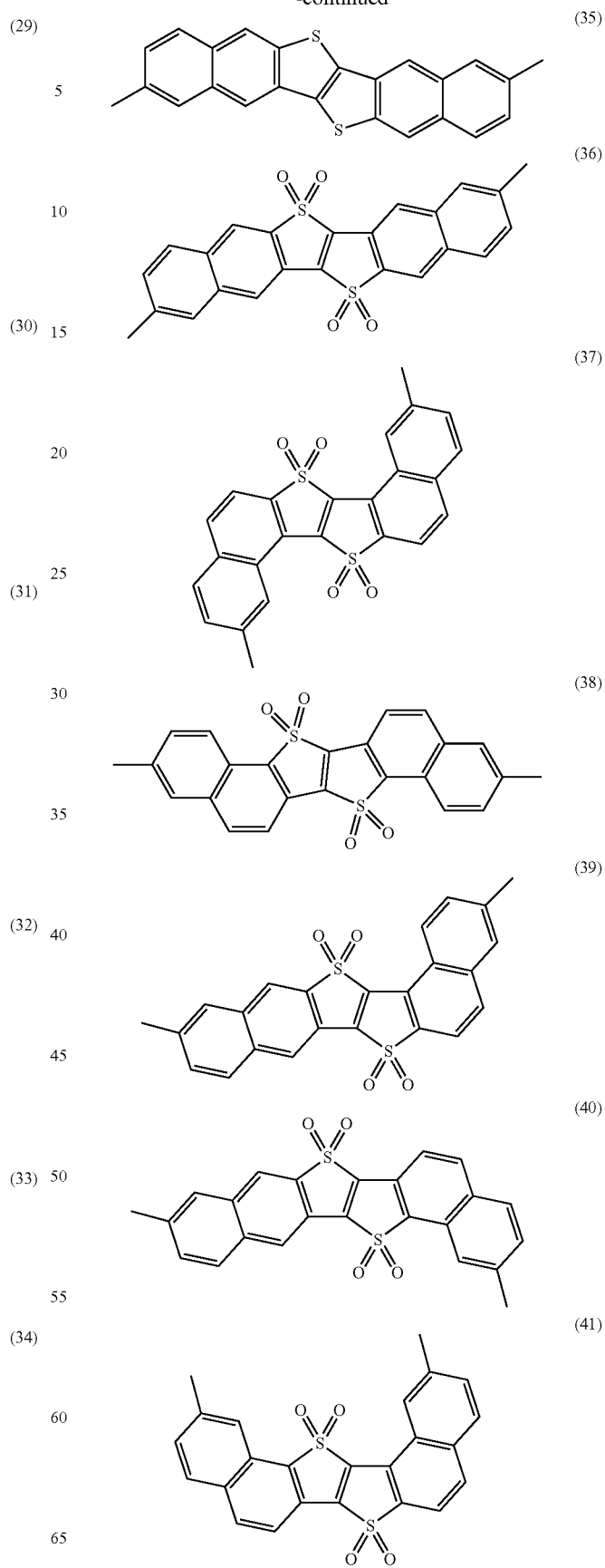

(42)

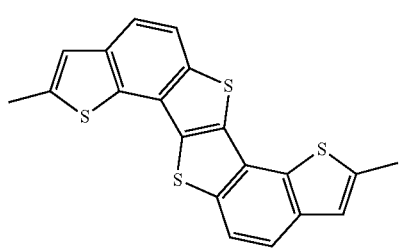

(44)

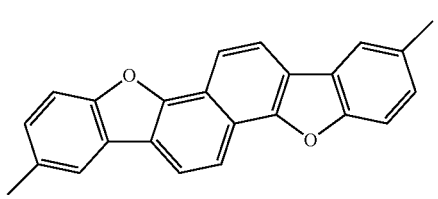

(43)

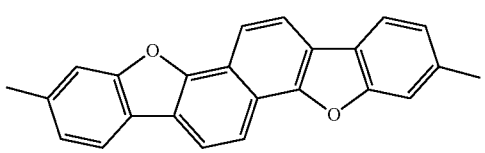

2. The organic transistor material according to claim 1, wherein the X is one selected from the group consisting of a chrysene skeleton, a benzothienobenzothiophene skeleton, a benzanthracene skeleton, and a dinaphthothienothiophene skeleton.

3. An organic transistor comprising an organic semiconductor layer containing the organic transistor material according to claim 1.

4. An organic transistor comprising an organic semiconductor layer containing the organic transistor material according to claim 2.

\* \* \* \* \*